United States Patent [19]

Narisada et al.

[11] Patent Number: 4,569,993
[45] Date of Patent: Feb. 11, 1986

[54] MALONYLOXACEPHEMCARBOXYLIC ACID DERIVATIVES

[75] Inventors: Masayuki Narisada, Osaka; Fumihiko Watanabe, Nara; Yoshio Hamashima, Kyoto, all of Japan

[73] Assignee: Shionogi & Co., Ltd., Osaka, Japan

[21] Appl. No.: 679,006

[22] Filed: Dec. 6, 1984

[30] Foreign Application Priority Data

Dec. 7, 1983 [JP] Japan .................. 58-232037

[51] Int. Cl.$^4$ ............................................. C07D 498/04
[52] U.S. Cl. ....................................... 544/90; 544/64; 544/69
[58] Field of Search ................ 544/90, 64, 69

[56] References Cited

U.S. PATENT DOCUMENTS

| | | | |
|---|---|---|---|
| 4,138,486 | 2/1979 | Narisada et al. | 544/90 X |
| 4,371,532 | 2/1983 | Narisada et al. | 544/90 X |
| 4,376,770 | 3/1983 | Narisada et al. | 544/90 X |
| 4,504,658 | 3/1985 | Narisada et al. | 544/90 |

*Primary Examiner*—Richard L. Raymond

*Attorney, Agent, or Firm*—Wenderoth, Lind & Ponack

[57] ABSTRACT

An antibacterial 7beta-substituted malonamido-7alpha-methoxy-3-tetrazolylthiomethyl-1-dethia-1-oxa-3-cephem-4-carboxylic acid and its derivative represented by the following formula:

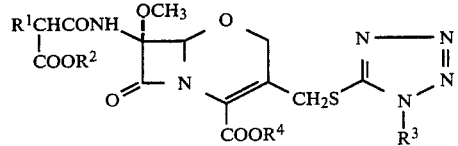

(wherein
$R^1$ is alkyl, hydroxyaryl, or thienyl;
$R^2$ and $R^4$ each is hydrogen, light metal or a carboxy-protecting group; and
$R^3$ is optionally protected hydroxyalkyl, carbamoylalkyl, dialkylaminoalkyl, or sulfamoylalkyl)
are disclosed.

4 Claims, No Drawings

MALONYLOXACEPHEMCARBOXYLIC ACID DERIVATIVES

This invention relates to a malonyloxacephemcarboxylic acid derivative. More specifically, it relates to 7beta-substituted malonamido-7alpha-methoxy-3-tetrazolylthiomethyl-1-dethia-1-oxa-3-cephem-4-carboxylic acid derivatives (I) represented by the following formula:

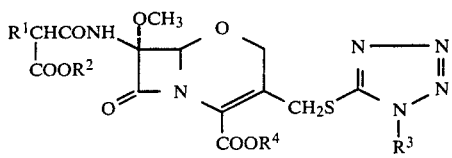

(wherein
R$^1$ is alkyl, hydroxyaryl, or thienyl;
R$^2$ and R$^4$ each is hydrogen, light metal or a carboxy-protecting group; and
R$^3$ is optionally protected hydroxyalkyl, carbamoylalkyl, dialkylaminoalkyl, or sulfamoylalkyl)

In the above formula (I), the alkyl represented by R$^1$ can preferably be 1C to 3C alkyl (e.g., methyl, ethyl, propyl) and the hydroxyaryl can preferably be hydroxyphenyl optionally substituted (e.g., by halogen), especially p-hydroxyphenyl.

The group represented by R$^3$ can be an optionally protected carbamoyl-, sulfamoyl-, di(1C to 3C)alkylamino-, or hydroxy-substituted 1C to 5C alkyl (especially ethyl).

The carboxy derivatives of Compound (I) include salts, esters, amides, and the like of the carboxy well known in the penicillin and cephalosporin chemistry. Thus, R$^4$ is either salt, ester, amide, or other function-forming group.

Typicals of them are light metal salts (e.g., lithium, sodium, potassium, magnesium, calcium, aluminum, or ammonium salt), organic base salts, for example, alkylamine salts (e.g., ethylamine, diethylamine, triethylamine, piperidine, morpholine, N-methylmorpholine salt), aromatic amine salts (e.g., aniline, dimethylaniline, naphthylamine salt), and aromatic base salts (e.g., pyridine, picoline, lutidine, nicotinamide, quinoline salt); physiologically acceptable salts, i.e., salts of light metal belonging to 1st to 3rd group and 2nd to 4th period of the Periodical Table (e.g., lithium, sodium, potassium, magnesium, calcium, aluminum); 1 to 8C aliphatic esters (e.g., methyl, ethyl, trichloroethyl, propyl, isopropyl, butyl, isobutyl, t-butyl, hexyl ester), 7 to 15C aralkyl esters (e.g., benzyl, methylbenzyl, dimethylbenzyl, methoxybenzyl, nitrobenzyl, diphenylmethyl, phenacyl, phthalidyl ester), 6 to 12C aromatic esters (e.g., phenyl, diisopropylphenyl, trichlorophenyl, pentachlorophenyl, indanyl ester), 3 to 12C silyl esters (e.g., trimethylsilyl, t-butyldimethylsilyl, dimethylmethoxysilyl ester), 3 to 12C stannyl esters (e.g., trimethylstannyl ester); physiologically acceptable esters, for example, 6 to 12C optionally substituted aryl esters (e.g., phenyl, xylyl, indanyl ester), 7 to 15C substituted aralkyl esters (e.g., phenacyl, phthalidyl ester), or substituted alkyl esters as 3 to 8C 1-alkanoyloxyalkyl (e.g., acetoxymethyl, propionyloxyethyl, pivaloyloxymethyl), 2 to 8C 1-alkoxyalkyl (e.g., methoxymethyl), 3 to 6C alkoxyformyloxyalkyl (e.g., 1-ethoxycarbonyloxyethyl), and 2-alkenyl (e.g., 4-methyl-2-oxo-1,3-dioxol-4-en-4-ylmethyl) esters; 6 to 12C N-hydroxyamino ester (ester with e.g., acetone oxim, acetophenone oxim, acetaldoxim, N-hydroxysuccinimide, N-hydroxyphthalimide), acid anhydrides, and amides or hydrazides of an equialent effect. The protective part may further be substituted. It is removed in the target compounds. So its structure can vary widely as far as the protection and deprotection are possible.

In above definitions, the alkyl part is straight, branched, or cyclic alkyl. The acyl part can be straight, branched, or cyclic and can be alkanoyl, alkenoyl, carbalkoxy, carbamoyl, sulfo, alkylsulfonyl, or sulfamoyl; or aroyl, aralkanoyl, arylalkenoyl, carbaralkoxy, arylsulfonyl, or the like, aryl part of which may optionally have a ring hetero atom (e.g., nitrogen, oxygen, sulfur), and be mono or di-cyclic.

The aryl part is mono- or di-cyclic and 5- or 6-membered aryl optionally having a hetero atom selected from nitrogen, oxygen, and sulfur in the nucleus. Typical heteroaromatic groups include pyrrolyl, furyl, thienyl, pyrazolyl, imidazolyl, oxazolyl, thiazolyl, triazolyl, oxadiazolyl, thiadiazolyl, tetrazolyl, oxatriazolyl, thiatriazolyl, pyridyl, pyronyl, thiopyronyl, pyrimidyl, pyrazinyl, pyridazinyl, triazinyl, indolyl, benzofuryl, benzothienyl, tetrazolopyridazinyl, purinyl, quinolinyl, isoquinolyl, pyridopyridyl, benzopyronyl, and the like.

The said groups may further have unsaturation and/or hetero atom.

The said groups can be substituted. Typical substituents include carbon functions (e.g., alkyl, alkenyl, alkylidene, alkynyl, aralkyl, aryl, carboxy, protected carboxy, carbamoyl, alkanoyl, alkenoyl, aralkanoyl, aroyl, aminoalkyl, cyano), nitrogen functions (e.g., amino, hydrazinyl, azido, diazo, alkylamino, arylamino, acylamino, alkylideneamino, imino, nitroso, nitro), oxygen functions (e.g., hydroxy, alkoxy, aralkoxy, aryloxy, acyloxy, oxo), sulfur functions (e.g., mercapto, alkylthio, arylthio, acylthio, thioxo, sulfinyl, sulfonyl, sulfo, protected sulfo), phosphorus functions (e.g., phospho, arylphosphonyl), halogens (e.g., fluorine, chlorine, bromine, iodine), and the like. These can have the same or different substituents. Two or more substituent can combine to form a ring. An instable substituents for production or use can be protected conventionally prior to the reaction and included in the definition of the substituent.

Typical protecting ggroups causing an unfavourable change during the reactions include a suitable hydrocarbyl, acyl, alkylated silyl, alkoxysilyl, alkylphosphinyl, or the like; for carboxy, sulfo, or the like include those forming ester, acid anhydride, amide, hydrazide, or the like. Especially preferable are those well known in the art as introduceable and removable without adverse effect on the other part of the molecule.

Especially useful substituents include alkyl, alkenyl, cyano, carboxy, protected carboxy, carboxyalkyl, hydroxyaminocarbonylalkyl, carbamoylalkyl, cyanoalkyl, aminoalkyl, ureidoalkyl, dialkylaminoalkyl, hydroxyalkyl, alkoxyalkyl, alkylthioalkyl, arylthioalkyl, haloalkyl, sulfamoylalkyl, alkoxysulfonylalkyl, alkylsulfonylalkyl, nitro, amino, hydroxy, alkyloxy, acyloxy, aryloxy, oxo, halogen, or the like. These can possess further conventional substituent and/or protecting group.

Compounds (I) are antibacterial against aerobic Gram-positive bacteria (e.g., *Bacillus cereus, Bacillus subtilis, Corynebacterium diphtheriae, Staphylococcus aureus, Staphylococcus epidermidis, Streptococcus pneumoniae, Streptococcus pyrogenes, Streptococcus viridans,* enterococci) and Gram-negative bacteria (e.g., *Citrobacter diversus, Citrobacter freundii, Enterobacter aerogens, Enterobacter cloacae, Escherichia coli, Haemophilus influenzae, Klebsiella pneumoniae, Neisseria gonorrhoeae, Neisseria meningitidis, Proteus mirabilis, Proteus morganii, Proteus vulgaris, Providencia rettgeri, Providencia stuartii, Pseudomonas aeruginosa, Salmonella paratyphi, Salmonella typhi, Serratia marcescens, Shigella sonnei, Yersinia enterocolitica*), including anaerobic bacteria (e.g., *Bacteroides fragilis, Clostridium difficile, Clostridium perfringens, Eubacterium lentum, Fusobacterium nucleatum,* Propionibacterium spp, peptostreptococci, Veillonella spp.).

They are bacteriocidal, bacteriostatic, disinfectant, or antiperishable agents and useful for treating or preventing human, veterinary, or poultry infections caused by sensitive Gram-positive bacteria or Gram-negative bacteria or some anaerobic bacteria. Further, they are useful as bacterial growth inhibitors on human, animal, plant, or perishable subjects, or as human or animal growth promoting additives in foodstuff.

Compounds (I) are stable and superior to other drugs in less side effects, broader antibacterial spectrum against resistant bacteria, in pharmacological characteristics (e.g., absorption, distribution, excretion, metabolism, disulfiram-like side reaction). Especially long and high blood level and anti-Gram-negative activity are remarkable.

This invention also provides a method for treating or preventing a human or veterinary bacterial infection (e.g., abscess, bronchitis, dermatitis, ear infections, empyema, enteritis, gastroenteritis, nasopharyngitis, osteomyelitis, pneumonitis, pneumonia, pustulosis, pyelonephritis, respiratory tract infections, rhinitis, septicemia, tonsillitis, ulceration, urinary tract infections, wound and soft tissue infections) caused by sensitive bacteria by administering an effective amount of Compound (I) at a typical daily dose of 10 micrograms to 1 gram externally, 0.2 to 5 gram intravenously, or 1 to 2 gram orally at an interval of 3 to 12 hours depending on the infecting bacteria and condition of the patient, if required formulating with a conventional additive.

Compound (I) as carboxylic acid or its light metal salt can be injected or infused intravenously, intramuscularly or subcutaneously (as e.g., injection, pellet), or given orally (as an oral preparation, e.g., capsule, dry syrup, emulsion, granule, powder, solution, suspension, tablet, troche), if required in admixture with an excipient (e.g., emulsifying agent). A pharmacological ester can be given intravenously, intramuscularly, subcutaneously, orally, externally, or topically (as e.g., ear, nasal, or ocular drug, ointment, inhalant, injection, pap preparation, spray, suppository).

Compound (I) is useful in various oral or parenteral dosage forms solely or in admixture with a coacting substance. The pharmaceutical composition may contain 0.01 to 99% of Compound (I) dissolved, dispersed, or suspended in a solid or liquid pharmaceutical carrier.

The composition can be a solid preparation (e.g., capsule, dry syrup, granule, pellet, pill, powder, suppository, troche, tablet), liquid preparation (e.g., dispersion, elixir, emulsion, inhalant, injection, ointment, suspension, syrup, solution from ampoule or vial containing crystals, lyophilizate, or powder), or the like. They can be flavored or colored, and capsules, granules, and tablets may be coated. They can be in a unit dosage form.

The carriers are harmless to both Compound (I) and patients and include among others, for a solid preparation, a binder (e.g., acacia, carboxymethylcellulose, gelatin, glucose, polyvinylpyrrolidone, sodium alginate, sorbitol, starch, syrup, tragacanth), bulking agent (e.g., bentonite, calcium carbonate, calcium phosphate, glycine, kaoline, lactose, polycarboxymethylene, sorbitol, starch, sugar, talc), diluent (e.g., calcium carbonate, kaolin, lactose, starch, sucrose), disintegrator (e.g., agar, carbonates, sodium laurylsulfate, starch), lubricant (e.g., boric acid, cacao oil, magnesium stearate, paraffin, polyethylene glycol, silica, sodium benzoate, stearic acid, talc), or wetting agent (e.g., hydroxypropyl cellulose); for solutions, a solvent (e.g., alcohol, buffer, methyl oleate, peanut oil, sesame oil, water), emulsifying agent (e.g., acacia, lethicin, sorbitan monooleate), suspending agent (e.g., aluminum stearate gel, carboxymethyl cellulose, gelatin, glucose, hydrogenated fats, hydroxyethylcellulose, methyl cellulose, sorbitol, sugar syrup), buffer, dispersing agent, or solubilizing agent; and for both, a preservative (e.g., methyl or ethyl p-hydroxybenzoate, sorbic acid), absorption promoter (e.g., glycerin mono- or di-octanoate), antioxidant, aromatic substace, analgesic, edible coloring agent, stabilizing agent, or the like.

All of above pharmaceutical preparations can be prepared in a conventional manner.

Compound (I) is also useful as a starting material for synthesizing other antibacterials or for testing sensitivity of bacteria.

Compound (I) may be synthesized, for example, as follows:

(1) Salt formation

Compound (I) having carboxy at position 4 or in the side chain conventionally forms a salt by the action of a base or by exchange reaction with a light metal salt or weak acid. For example, the free acid is neutralized with light metal hydrogencarbonate, or treated with a alkali metal lower carboxylate salt in a polar organic solvent (e.g., alcohol, ketone, ester), and then adding less dissolving solvent or concentrating to separate the objective salt. The reaction time is usually 1 to 10 minutes at lower than 50° C., but it may be longer, if no side reaction occurs.

Antibacterial salts thus produced are isolated as solid (e.g., crystals, powders) or alternatively by lyophilizing and are formulated conventionally, if required with a conventional additives.

(2) Deprotection of protected carboxy

Deprotection of a carboxy-protected Compound (I) gives a free Carboxy compound (I), by a conventional handling, e.g., as follows:

(a) A highly reactive ester, amide, or anhydride can be removed with an aqueous acid, base, buffer solution, or ion exchange resin. Some insufficiently reactive esters can easily be removed after conventional activating (e.g., a trichloroethyl ester with metal and acid and a p-nitrobenzyl ester with hydrogenation or dithionate).

(b) An aralkyl ester can be removed by conventional hydrogenating over a catalyst.

(c) An aralkyl, cyclopropylmethyl, sulfonylethyl, aralkyl, etc. ester can be removed by treating with a mineral acid, Lewis acid (aluminum chloride, stannic chloride, titanum tetrachloride), sulfonic acid (e.g., methanesulfonic acid, trifluoromethanesulfonic acid), or strong carboxylic acid (e.g., trifluoroacetic acid), if required in the presence of a cation scavenger.

(d) A phenacyl, alkenyl, hydroxyaralkyl, or the like ester can be removed with a base or nucleophilic reagent. A photochemically reactive phenacyl esters can be removed by irradiating.

(e) A 2-alkenyl ester is removed with alkali metal alkanoate and palladium-triphenylphosphine to recover in a form of alkali metal salt.

(f) and other various carboxy deprotections.

(3) Introduction of the 3-substituent

Compound (I) but having a leaving group-substituted methyl at position 3 is treated with the corresponding heteroaromatic thiol or its reactive derivative giving an objective Compound (I). Reactive halogen, sulfonyloxy, alkanoyloxy, dihaloacetoxy, trihaloacetoxy, and the like are typical leaving groups. An alkali metal salt, ammonium salt, carboxylate ester or the like is typical reactive derivative of Thiol (V). This reaction is carried out at 0° C. to 60° C. in an aqueous or anhydrous solvent and promoted by a dehydrating reagent, phosphoryl chlorides, thiocyanate, or the like.

(4) Amidation

A reaction of Amine (II) or its reactive derivative with Carboxylic acid (III) or its reactive derivative gives Amide (I) or its derivatives.

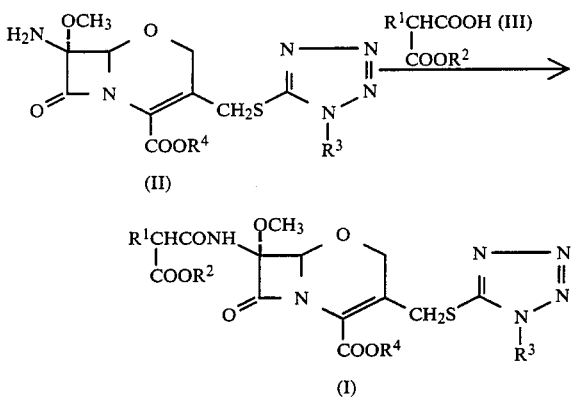

Typical reactive derivatives of Amine (II) have 7-amino activated by silyl (e.g., trimethylsilyl, methoxydimethylsilyl, t-butyldimethylsilyl), stannyl (e.g., trimethylstannyl), alkylene (as a part of enamino from the amino with a carbonyl compound, e.g., aldehyde, acetone, acetylacetone, acetoacetate, acetoacetonitrile, acetoacetanilide, cyclopentanedione, acetylbutyrolactone), alkylidene (e.g., 1-haloalkylidene, 1-haloaralkylidene, 1-alkoxyalkylidene, 1-alkoxyaralkylidene, 1-alkoxy-1-phenoxyalkylidene, alkylidene, aralkylidene), acid (as a salt of the amino with e.g., mineral acid, carboxylic acid, sulfonic acid), easily removable acyl (e.g., alkanoyl), or the like, or that protected at other function of the molecule.

The reactive derivatives of Acid (III) include acid anhydride, halide, reactive ester, reactive amide, azide, and other conventional derivatives for acylation.

The amidating agent and the procedure for using it are, e.g., as follows:

(a) Free acid (III)

This is used in the presence of a condensing reagent [carbodiimide (e.g., N,N'-diethylcarbodiimide, N,N'-dicyclohexylcarbodiimide), carbonyl compound (e.g., carbonyldiimidazole), isoxazolinum salt, acylamino compound (e.g., 2-ethoxy-1-ethoxycarbonyl-1,2-dihydroquinoline), amidase or the like]. Amine (II) or its reactive derivative, 1 to 2 molar equivalents of the condensing reagent, and 1 to 2 molar equivalents of Acid (III) are reacted preferably in an aprotic solvent (e.g., halohydrocarbon, nitrile, ether, amide solvent or the mixture).

(b) Acid anhydride

This is a symmetric anhydride, mixed anhydride [with a mineral acid (e.g., phosphoric acid, sulfuric acid, carbonic half ester) or organic acid (e.g., alkanoic acid, aralkanoic acid, sulfonic acid, intramolecular acid anhydride (e.g., ketene, isocyanate), or acid halide (a mixed anhydride with hydrogen halide)] of Acid (III).

Preferably, Amine (II) or its reactive derivative, 1 to 2 molar equivalents of the acid anhydride, and 0 to 10 molar equivalents of an acid scavenger [for example, inorganic base (e.g., oxide, hydroxide, carbonate, or hydrogen carbonate of alkali metal or alkaline earth metal), organic base (e.g., tertiary amine, aromatic base), oxirane (e.g., alkylene oxide, aralkylene oxide), pyridinium salt (e.g., tripyridiniumtriazine trichloride), adsorbent (e.g., Celite), or the like] are mixed preferably in an aprotic solvent (e.g., halohydrocarbon, nitrile, ether, amide, or a mixture) or under the Schotten-Baumann reaction condition.

(c) Acid halide

This is a mixed anhydride of hydrogen halide with Acid (III). Preferably, Amine (II) or its reactive derivative is reacted as above with preferably 1 to 2 molar equivalents of the acid halide in the presence of 1 to 10 molar equivalents of said acid scavenger in a solvent (especially e.g., halohydrocarbon, nitrile, ether, ester, ketone, dialkylamide, water, or a mixture) or under the Schotten-Baumann reaction condition.

(d) Reactive ester

This is an enol ester (e.g., vinyl ester, isopropenyl ester), aryl ester (e.g., phenyl ester, halophenyl ester, nitrophenyl ester), heterocyclic ester (e.g., pyridyl ester, benzotriazole ester), imidoyl ester (succinimidoyl ester, phthalimidoyl ester, isopropylideneimidoyl ester), thiol ester (e.g., aralkylthiol ester, tetrazolylthiol ester); or the like acylating reagent having a conventional reactive ester grouping. This is handled as written below. An enzymatically reactive ester (e.g., lower alkyl ester) may conventionally be used in an aqueous solvent in the presence of an amidase.

(e) Reactive amide

This is an aromatic amide (e.g., amide with imidazole, triazole, or 2-ethoxy-1,2-dihydroquinoline), diacylanilide, or the like amide of Acid (III) handled as given below.

(f) Formimino compound

This is an N,N-dimethylformimino ester halide or the like of Acid (III).

The reactions from (d) to (f) are usually carried out by mixing 1 molar equivalent of Amine (II) or its reactive derivative, 1 or 2 molar equivalents of Carboxylic acid (III) derivative at −20° C. to 40° C. for 1 to 5 hours in an aprotic solvent (e.g., halohydrocarbon, ether, ketone, nitrile, ester, amide, or a mixture).

(5) Methoxylation

Compound (I) having no methoxy at position 7 is treated with an N-halogenating reagent, dehydrohalogenating reagent, and methanol, successively to give the corresponding 7beta-amido-7alpha-methoxy compound (I) regardless of the starting 7-hydrogen stereochemistry.

The reaction is handled as follows:
(a) Reacting with alkyl hypochlorite (e.g., t-butyl hypochlorite) and alkali metal methoxide (e.g., lithium methylate, sodium methylate) in methanol.
(b) Reacting with molecular halogen and a base (e.g., metal alkoxide - - - lithium methoxide, sodium methoxide, magnesium methoxide, etc. - - - , DBU, triethylamine, picoline) in methanol.
(c) Reacting with an N-halogenating agent, (e.g., hypohalite ester, N-haloamide, N-haloimide, or the like), dehydrohalogenating reagent (e.g., alkali metal alkoxide, aryl alkali metal), and then methanol.
(d) Other conventional methods.

(6) Protection of carboxy and other reactive functions

When Compound (I) is subjected to a chemical reaction as above to make other Compound (I), reactive functional groups other than the reacting group are sometimes conventionaly protected previously. In this case, conventional methods in the art according to the type of functional groups are used as described in various literatures.

These protection and deprotection of reactive groups are given in J. F. W. McOmie Ed., "Protective Groups in Organic Chemistry", pp. 183 (1973), Plenum Press, N.Y.; S. Patai Ed., "The Chemistry of Functional Groups", pp 505 (1969), Interscience Publ., John Wiley & Sons, Ltd., London; and Flynn Ed. "Cephalosporins and Penicillins", Academic press, N.Y. (1972), and various patent literatures.

Typical protections are, e.g., acylation and etherification for hydroxy; e.g., acylation, enamine formation, and silyl introduction for amino; and e.g., esterification, amidation, and acid anhydride formation, for carboxy. A physiologically active ester formation to change pharmacological characteristics is one of this protection. For this purpose, Carboxylic acid (I) is treated with a base to form a salt which is then treated with halide of the desired ester forming group to obtain the objective Compound (I).

(7) Reaction conditions

The said reactions from (1) to (6) are usually carried out at −30° C. to 100° C., preferably at −20° C. to 50° C. for 10 minutes to 10 hours, if required in an anhydrous condition.

Typical reaction solvents include a hydrocarbon (e.g., pentane, hexane, octane, benzene, toluene, xylene), halohydrocarbon (e.g., dichloromethane, chloroform, carbon tetrachloride, dichloroethane, trichloroethane, chlorobenzene), ether (e.g., diethyl ether, methyl isobutyl ether, dioxane, tetrahydrofuran), ketone (e.g., acetone, methyl ethyl ketone, cyclohexanone), ester (e.g., ethyl acetate, isobutyl acetate, methyl benzoate), nitrohydrocarbon (e.g., nitromethane, nitrobenzene), nitrile (e.g., acetonitrile, benzonitrile), amide (e.g., formamide, acetamide, dimethylformamide, dimethylacetamide, hexamethylphosphorotriamide), sulfoxide (e.g., dimethylsulfoxide), carboxylic acid (e.g., formic acid, acetic acid, propionic acid), organic base (e.g., diethylamine, triethylamine, pyridine, picoline, collidine, quinoline), alcohol (e.g., methanol, ethanol, propanol, hexanol, octanol, benzyl alcohol), water, and other industrial solvents and mixture thereof.

(8) Work up

The objective products are obtained from each reaction mixture by removing contaminants (e.g., unreacted starting materials, by-products, solvents) conventionally (e.g., by extracting, evaporating, washing, concentrating, precipitating, filtrating, drying) and purified by usual work up (e.g., adsorbing, eluting, distilling, precipitating, separating, chromatographying, etc.).

(9) Examples

Following examples illustrate the embodiments of this invention.

Physicochemical constants of the products are summarized in the tables. In the Examples, values of IR show frequency in cm$^{-1}$, NMR show chemical shifts in ppm, and of J show coupling constant in cps. "Part" shows part by weight and "equivalent" shows molar equivalents to the starting beta-lactam.

Work-up procedure is usually as follows: A reaction mixture is, if required after addition of a solvent (e.g., water, acid, dichloromethane) and taking oranic layer, washed with water, dried and concentrated. Concentrating is done in vacuum. Residue is crystallized, precipitated, or filtrated to obtain the product, if required after silica gel chromatography. Physical constants of the product are identified with those of samples produced by an alternative route, when available.

(Abbreviations)

BH=diphenylmethyl, Ph=phenyl, PMB=p-methoxybenzyl.

EXAMPLE 1

(Sodium salt, preparation, use)

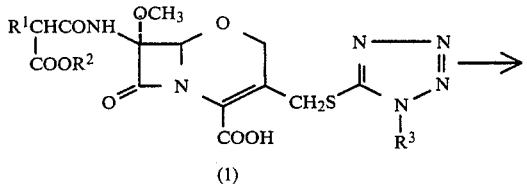

(1)

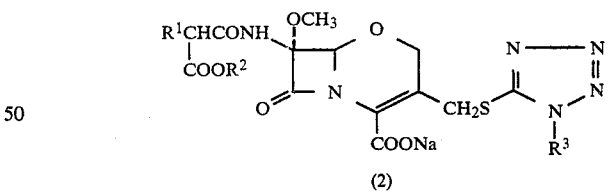

(2)

A solution of Carboxylic acid (1) (1 g) in aqueous 0.5% sodium hydrogen carbonate (5 ml) adjusted to pH 7 with hydrochloric acid is washed with ethyl acetate, desalted, and poured into a 10 ml vial. This is lyophilized conventionally to give the corresponding sodium salt (2) as powder.

The sodium salt (1 g) produced as above under sterile condition is dissolved in sterile water (4 g) is given twice a day intravenously to a patient suffering from Staphylococcus aureus infection for treating said disease.

The sodium salt (2) is assayed for the minimal inhibitory concentration by the standard method of the Japan Society of Chemotherapy to give values of less than 10 microgram/ml against Streptococcus pyogenes C-203 and

EXAMPLE 2

(Deesterification)

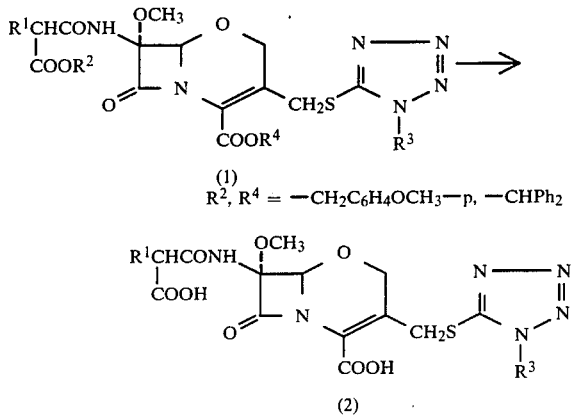

(1) A solution of p-methoxybenzyl or diphenylmethyl ester (1) (1 part) in a mixture of dichloromethane (0.3 to 3 parts), trifluoroacetic acid (0.3 to 3 parts), and anisole (0.5 to 5 parts) is stirred for 10 minutes to 3 hours at between −10° and 40° C. The solution is concentrated in vacuum to remove the solvent and reagent. The residue is washed with benzene to give the corresponding free acid in 70 to 90% yield.

(2) To a solution of the said ester (1) (1 part) in a mixture of dichloromethane (5 to 9 parts) and anisole (2 to 8 parts) is added aluminum chloride or titanium tetrachloride (2 to 4 equivalents) at between −10° and 10° C., and the mixture is stirred for 1 to 3 hours. The mixture is washed with diluted hydrochloric acid and water, dried and concentrated to give the corresponding free acid in 80 to 95% yield.

EXAMPLE 3

(Amidation)

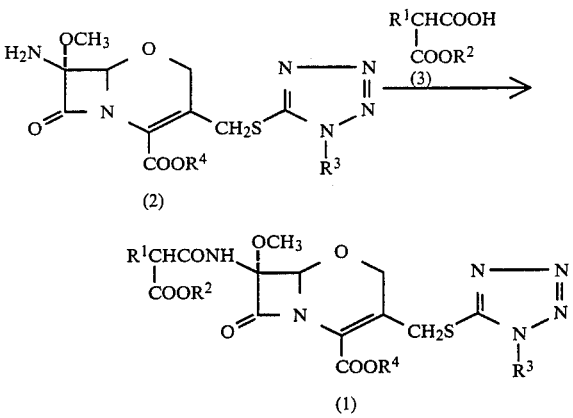

A 7beta-Amino compound (2) (1 equivalent) is treated with Carboxylic acid corresponding to the 7beta-side chain (3) or its reactive derivative to give Amide (1), for example, by a method as exemplified below:

(1) In a mixture of dichloromethane (10 volumes), 2-ethoxy-1-ethoxycarbonyl-1,2-dihydroquinoline (1.1 equivalents), N,N'-dicyclohexylcarbodiimide (1.1 equivalents), pyridine (1.5 equivalents), and Carboxylic acid (3) (1.1 equivalents), stirred for 1 to 6 hours at 0° C. to room temperature.

(2) In a mixture of ethyl acetate (10 volumes), di-2-pyridyl disulfide (1.1 equivalents), triphenylphosphine (1.1 equivalents), and Carboxylic acid (3) (1.1 equivalents), stirred for 2 to 6 hours at 10° to 50° C.

(3) In a mixture of dichloromethane (3 volumes), 1,3,5-tripyridiniumtriazine trichloride (4 equivalents), and Carboxylic acid (3) (1.1 equivalents), stirred for 1 to 5 hours at −10° to 10° C.

(4) In a mixture of carbon tetrachloride (30 volumes), 4-methylmorpholine (1.5 equivalents), trisdiethylaminophosphine (1.1 equivalents) and Carboxylic acid (3) (1.1 equivalents), kept at −20° to 10° C. for 1 to 5 hours.

(5) In a mixture of chloroform (10 volumes) and dimethoxyethane (10 volumes), triethylamine (1.5 moles), and a mixed anhydride of Carboxylic acid (3) and isobutoxyformic acid, stirred at a temperature between −5° to 10° C. over a 30 minutes to 6 hours.

(6) In a mixture of ethyl acetate (10 volumes), 1,2-dichloroethane (10 volumes), 4-methylmorpholine (1.5 equivalents), and the symmetric anhydride of Carboxylic acid (3) (1.1 equivalents), refluxed for 10 minutes to 2 hours.

(7) In a mixture of dichloromethane (10 volumes), pyridine (1.5 equivalents), and mixed anhydride of Carboxylic acid (3) and methanesulfonic acid (1.1 equivalents), stirred for 1 to 3 hours warming at from 0° C. to room temperature.

(8) In a mixture of ethyl acetate (10 volumes), pyridine (1.5 equivalents) and a mixed anhydride of diethyl hydrogen phosphate and Carboxylic acid (3) (1.5 equivalents), stirred at 0° C. to 10° C. for 1 to 5 hours.

(9) In a mixture of ethyl acetate (10 volumes), dichloromethane (10 volumes), 4-methylmorpholine (1 equivalent), and mixed anhydride of Carboxylic acid (3) and dichlorophosphoric acid (1.1 equivalents), stirred for 1 to 3 hours at 0° C. to room temperature.

(10) In a mixture of lutidine (1.5 equivalents), dichloromethane (10 volumes), and the mixed anhydride (1.1 to 2 equivalents) of Carboxylic acid (3) and monochlorophosphoric acid dimethylamide, stirred for 1 to 4 hours at 0° to 30° C.

(11) In a mixture of dichloromethane (5 volumes), trifluoroacetic anhydride (1.5 equivalents), pyridine (3 equivalents), and Carboxylic acid (3) (1.5 equivalents), stirred for 1 to 5 hours at 0° C. to room temperature.

(12) In a mixture of dichloromethane (10 volumes), bromide of diethyl hydrogen phosphate (1.2 equivalents), 4-methylmorpholine (2.5 equivalents), and Carboxylic acid (3) (1.2 equivalents), stirred for 1 to 3 hours at 0° C. to room temperature.

(13) Amine (2) having carboxy at position 4 of cephem ring is dissolved in aqueous (10 volumes) sodium hydrogen carbonate (2.5 equivalents). Carboxylic acid (3) chloride (1.1 equivalents) is dropwise added thereto. The mixture is kept at −5° C. to room temperature for 30 minutes to 2 hours.

(14) Amine (2) having carboxy at position 4 of cephem ring is treated with trimethylsilyl chloride and triethylamine (1.2 equivalents each), and then treated with pyridine (4 equivalents) and Carboxylic acid (3) chloride (1.1 equivalents) at −30° C. for between 30 minutes and 2 hours, and then the resulting silyl ester is hydrolyzed with acid.

(15) In a solution of picoline (4 equivalents) and Carboxylic acid (3) chloride (1.2 equivalents) in dichlorodichloromethane (20 volumes), stirred at 0° C. to −30° C. over 30 minutes and 2 hours.

(16) In a mixture of dimethylformamide (2 volumes), ethyl acetate (10 volumes), triethylamine (1.1 equivalents), and Carboxylic acid (3) chloride (1.1 equivalents), stirred at 0° C. to −20° C. for between 30 minutes and 3 hours.

(17) In a mixture of dichloromethane (30 volumes), cyanuric chloride (1.1 equivalents), pyridine (4 equivalents), and Carboxylic acid (3) (1.1 equivalents), stirred for 30 minutes to 2 hours at −30° C. to 10° C.

(18) In a mixture of dichloromethane (3 volumes), phosphorus oxychloride (1.1 equivalents), triethylamine (1.5 equivalents), and Carboxylic acid (3) (1.1 equivalents), stirred for 20 minutes to 2 hours at −10° C. to 10° C.

(19) Amine (2) is treated with trimethylsilyl chloride and an acid scavenger, and this is treated with phosphorus oxychloride (1.5 equivalents), Carboxylic acid (3) (1.2 equivalents), and dimethylaniline (4 equivalents) in dichloromethane (5 parts) for 30 minutes to 2 hours at 0° C. to room temperature.

(20) In a mixture of dichloromethane (8 volumes), thionyl chloride (1.5 equivalents), pyridine (2.5 equivalents), and Carboxylic acid (3) (1.1 equivalents), stirred for 1 to 5 hours at −30° to 0° C.

(21) In a mixture of chloroform (3 volumes), toluene (1 volume), picoline (2 equivalents), oxalyl chloride (1 equivalent), and Carboxylic acid (3) (1.1 equivalents), stirred for 10 minutes to 2 hours at −50° C. to 10° C.

(22) In a mixture of dichloromethane (20 volumes), pyridine (3 equivalents), N,N'-dicyclohexylcarbodiimide (3 equivalents), and 1-benzotriazolyl ester of Carboxylic acid (3) (3 equivalents), stirred for 5 to 30 hours at 10° to 50° C.

(23) In a mixture of dichloromethane (20 volumes), 1-ethoxycarbonyl-2-ethoxy-1,2-dihydroquinoline (2.1 equivalents), and Carboxylic acid (3) (2 equivalents), stirred at room temperature for 1 to 15 hours.

(24) In a mixture of dioxane (10 volumes), and phthalimidoyl ester of Carboxylic acid (3) (2 equivalents), stirred for 2 to 8 hours at 10° to 50° C.

(25) In a mixture of methyl isobutyl ketone (10 volumes) and succinimidoyl ester of Carboxylic acid (3) (1.5 equivalents), stirred for 2 to 9 hours at 0° to 40° C.

(26) In a mixture of carbonyldiimidazole (1.1 equivalents), tetrahydrofuran (10 volumes), dimethylacetamide (5 volumes), and Carboxylic acid (3) (1.1 equivalents), stirred for 1 to 5 hours at 0° C. to room temperature.

(27) In a mixture of dimethylformamide (5 volumes), dimethylaniline (1.3 equivalents), Carboxylic acid (3), and the Vilsmeyer reagent made from dimethylformamide (1.1 equivalents), stirred at room temperature for 1 to 5 hours.

(28) In a mixture of dichloromethane (10 volumes), dimethylformamide (5 volumes), N,N'-dicyclohexylcarbodiimide (1.1 equivalents), picoline (1.2 equivalents), and Carboxylic acid (3) (1.1 equivalents), heated for 2 hours to 24 hours.

EXAMPLE 4

(Methoxylation)

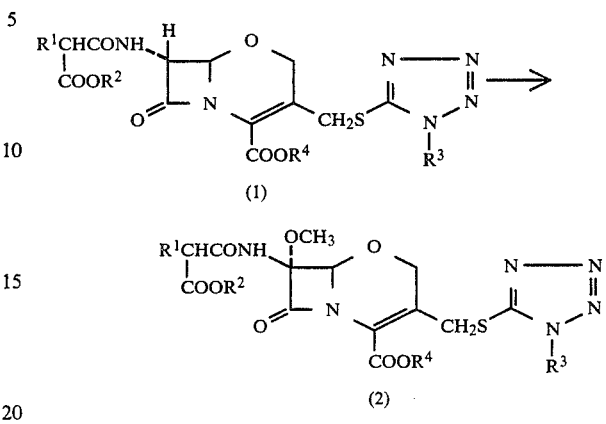

To a solution of 7alpha-amido-3-substituted methyl-1-dethia-1-oxa-3-cephem-4-carboxylic acid derivative (1) (1 part) in dichloromethane (10 parts) is added tert-butyl hypochlorite (1.1 equivalent). After standing for 3 hours at −20° C., a solution of lithium methoxide (1.2 equivalents) in methanol is added to the mixture and let react for 30 minutes. The reaction mixture is acidified with acetic acid and diluted with dichloromethane. This is washed with water, dried, and concentrated to give the corresponding 7beta-amido-7alpha-methoxy-3-substituted methyl-1-dethia-1-oxa-3-cephem-4-carboxylic acid derivative (2) in 40 to 85% yield.

EXAMPLE 5

(Heterothio introduction at position 3)

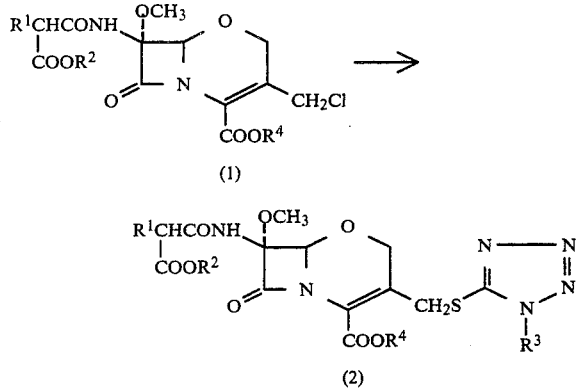

(1) A solution of 3-chloromethyl compound (1) (1 part), heterocyclic thiol sodium salt (1.2 equivalents), tetrabutylammonium bromide (trace amount) in dichloromethane (10 to 20 parts), and water (1 to 5 parts) is stirred for 30 minutes to 3 hours at room temperature. The organic layer is washed with water, dried, and concentrated to give the corresponding heterocyclic thio compound (2). Yield: 80 to 90%.

(2) A solution of 3-chloromethyl compound (1) (1 part) and heterocyclic thiol sodium salt (1.2 equivalents) in dimethylformamide (3 to 5 parts) is stirred for 30 minutes to 3 hours. The solution is poured into water and extracted with ethyl acetate. The extract is washed with water, dried, and concentrated to give the corresponding heterocyclic thio compound (2). Yield: 80 to 90%.

EXAMPLE 6

(Pharmacologically acceptable esters)

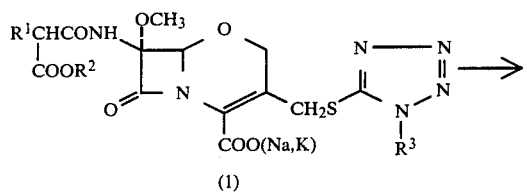

(1)

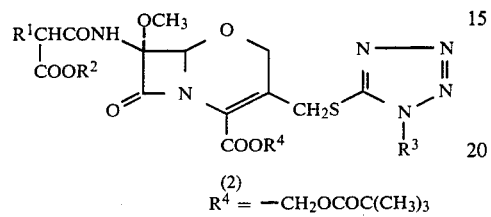

(2)
$R^4 = -CH_2OCOC(CH_3)_3$ (1) To a solution of Carboxylic acid potassium salt (1) (1 millimole) in N,N-dimethylformamide (2 to 5 parts) is added iodomethyl pivalate (1 to 2 equivalents) under ice cooling. After 15 minutes to 2 hours' stirring, the mixture is diluted with ethyl acetate, washed with ice water and aqueous sodium hydrogen carbonate, dried, and concentrated. The residue is crystallized from ethyl acetate to give the pivaloyloxymethyl ester (2).

(2) The potassium salt of above section (1) is replaced by sodium salt to give the same products under same condition.

(3) The pivaloyloxymethyl ester (2) of above section (1) (250 mg), corn starch (150 mg), and magnesium stearate (5 mg) are mixed, granulated, and encapsulated in a conventional manner. This capsule (1 to 3 capsules) is given orally thrice a day to treat a patient suffering from infection caused by sensitive Staphylococcus aureus.

EXAMPLE 7

(Deprotection)

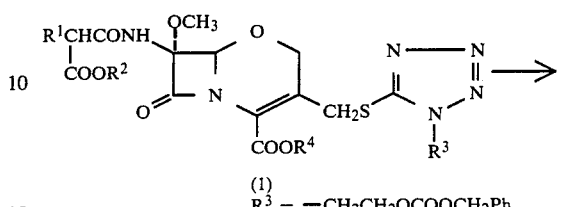

(1)
$R^3 = -CH_2CH_2OCOOCH_2Ph$

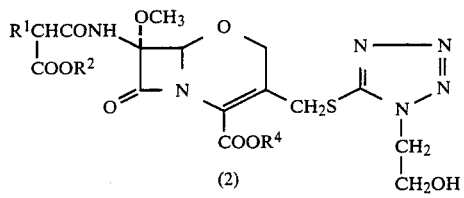

(2)

(1) Benzyloxyformyl ester (1) (1 part), trifluoroacetic acid (0.3 to 3 part), and anisole (0.5 to 5 parts) is let react in dichloromethane (0.3 to 3 parts) at $-10°$ C. to 40° C. for 10 minutes to 3 hours. The reaction mixture is concentrated to remove the solvent and reagent. Resulting material is washed with benzene to afford the corresponding alcohol (2) in 70 to 90% yield.

(2) The said starting material (1) (1 part) in a mixture of dichloromethane (5 to 9 parts) and anisole (2 to 8 parts) is treated with aluminum chloride or titanium tetrachloride (2 to 4 equiv.) for 1 to 3 hours. The reaction mixture is washed with diluted hydrochloric acid and water, dried and concentrated to give the corresponding alcohol (2) in 80 to 90% yield.

TABLE I

Structure:
R¹CHCONH-[β-lactam with OCH₃]-CH₂S-C(COOR⁴)=... with N=N-N-R³ tetrazole-like; COOR²

| Compd. No. | R¹ | R² | R³ | R⁴ | IR ν(cm⁻¹) | NMR δ(ppm) |
|---|---|---|---|---|---|---|
| 1 | $C_2H_5$ | H | $CH_2CH_2OH$ | H | KBr: 3400, 1780, 1720, 1630, 1520 | CD₃OD: 0.94 (t, J = 7Hz, 3H); 1.87 (dq, J = 7Hz, J = 7Hz, 2H); 3.6 (br s, 1H); 3.52 (s, 3H); 3.92 (t, J = 5Hz, 2H); 4.27 (s, 2H); 4.41 (t, J = 5Hz, 2H); 4.57 (s, 2H); 5.01, 5.04 (2 × s, 1H) |
| 2 | $C_2H_5$ | BH | $-CH_2CH_2O-PhCH_2OCO$ | BH | CHCl₃: 3400, 1790, 1750, 1719, 1497 | CDCl₃: 0.89 (t, J = 7Hz, 3H); 1.99 (dq, J = 7Hz, J = 7Hz, 2H); 3.33 (t, J = 7Hz, 1H); 3.39 (s, 3H); 4.15 (d, J = 15Hz, 1H); 4.30 (d, J = 15Hz, 1H); 4.40 (s, 4H); 4.45 (s, 2H); 4.97 (s, 1H); 5.07 (s, 2H); 6.89 (s, 2H); 7.2~7.7 (m, 25H) |
| 3 | $C_2H_5$ | H | $CH_2CH_2N(CH_3)_2$ | H | KBr: 3200, 2600, 1785, 1670 | |
| 4 | $C_2H_5$ | BH | $CH_2CH_2N(CH_3)_2$ | BH | CHCl₃: 3400~3300, 1787, 1718 | CDCl₃: 0.92 (t, J = 7Hz, 3H); 2.01 (dq, J = 7Hz, J = 7Hz, 2H); 2.17 (s, 6H); 2.65 (t, J = 6Hz, 2H); 3.33 (t, J = 7Hz, 1H); 3.38 (s, 3H); 4.15 (t, J = 6Hz, 2H); 4.23 (s, 2H); 4.47 (s, 2H); 4.97 (s, 1H) |

TABLE I-continued $$R^1CHCONH \underset{COOR^2}{|} \overset{OCH_3}{\underset{O}{\overset{|}{\diagup}}} \underset{\underset{COOR^4}{CH_2S}}{\overset{N-N}{\underset{N-R^3}{\parallel}}}$$

| Compd. No. | R[1] | R[2] | R[4] | R[3] | IR $\nu$(cm$^{-1}$) | NMR $\delta$(ppm) |
|---|---|---|---|---|---|---|
| 5 | C$_2$H$_5$ | CH$_2$OCOC(CH$_3$)$_3$ | CH$_2$OCOC(CH$_3$)$_3$ | CH$_2$CH$_2$N(CH$_3$)$_2$.HCl | KBr: 3400 2600~ 2400 1788 1752 1700 | CD$_3$COCD$_3$: 0.95 (t, J = 7Hz, 3H) 1.17 (s, 9H) 1.21 (s, 9H) 1.88 (dq, J = 7Hz, J = 7Hz, 2H) 2.98 (s, 6H) 3.46 (s, 3H) 3.60 (t, J = 7Hz, 1H) 3.81 (t, J = 7Hz, 2H) 4.25, 4.47 (ABq, J = 14Hz, 2H) 4.70 (s, 2H) 4.93 (t, J = 7Hz, 2H) 5.11, 5.14 (2 × s, 1H) 5.76 (s, 2H) 5.82, 6.03 (2 × d, J = 6Hz, 2H) 6.91 (s, 2H) 7.1~7.6 (m, 10H) |
| 6 | C$_2$H$_5$ | CH$_2$OCOC(CH$_3$)$_3$ | CH$_2$OCOC(CH$_3$)$_3$ | CH$_2$CH$_2$N(CH$_3$)$_2$ | CHCl$_3$: 3400~ 3300 1792 1755 1700 | |
| 7 | HO—⟨phenyl⟩—CH$_2$— | Na | Na | CH$_2$CH$_2$OH | KBr: 3400 1766 1669 1600 1513 | CD$_3$OD: 3.33, 3.40 (2 × s, 3H) 3.88 (t, J = 5Hz, 2H) 4.30 (t, J = 5Hz, 2H) 4.30 (s, 2H) 4.47 (s, 2H) 4.98 (s, 1H) 6.68 (A$_2$B$_2$, A - part, J = 8Hz, 2H) 7.17 (A$_2$B$_2$, B - part, J = 8Hz, 2H) |

TABLE I-continued structure:
$R^1CHCONH$ with $COOR^2$, $OCH_3$, β-lactam ring with N, O linkage, $CH_2S$-, $COOR^4$, tetrazole ring ($N=N-N-N-R^3$)

| Compd. No. | R¹ | R² | R⁴ | R³ | IR ν(cm⁻¹) | NMR δ(ppm) |
|---|---|---|---|---|---|---|
| 8 | 4-hydroxyphenyl | H | H | CH₂CH₂OH | NuJol: 3280, 1780, 1718, 1614, 1515, 1452 | CD₃COCD₃: 3.37, 3.47 (2 × s, 3H); 3.97 (t, J = 5Hz, 2H); 4.33 (s, 2H); 4.72 (s, 1H); 5.07 (s, 1H); 6.67 (br, 4H); 6.79 (A₂B₂, A - J = 8Hz, 2H); 7.27 (A₂B₂, B - J = 8Hz, 2H); 8.33 (m, 1H) |
| 9 | 4-hydroxyphenyl | PMB | BH | CH₂CH₂OH | CHCl₃: 3350, 1788, 1720, 1612 | CDCl₃: 3.45 (s, 3H); 3.70 (s, 3H); 3.83~4.52 (m, 8H); 4.93 (s, 1H); 5.05 (s, 2H) |
| 10 | 4-hydroxyphenyl | PMB | BH | CH₂CH₂OCOPhCH₂O | CHCl₃: 3595, 3405, 3330, 1789, 1750, 1720, 1614, 1513 | CDCl₃: 3.43, 3.47 (2 × s, 3H); 3.73 (s, 3H); 4.13 (s, 2H); 4.38 (br s, 6H); 4.50, 4.52 (2 × s, 1H); 4.97 (s, 1H); 5.07 (s, 4H); 6.11~8.00 (m, 26H) |
| 11 | 4-hydroxyphenyl | H | H | CH₂CONH₂ | Nujol: 3300, 1780, 1690 | CDCl₃ + CD₃OD: 3.47 (s, 3H); 4.27 (br s, 2H); 5.07 (br s, 3H); 6.65~7.42 (m, 4H) |

TABLE I-continued

[Structure: R¹CHCONH-(OCH₃)-β-lactam-CH₂S-C(=N-N=N-NR³)-COOR⁴, with COOR² on the α-carbon]

| Compd. No. | R¹ | R² | R⁴ | R³ | IR ν(cm⁻¹) | NMR δ(ppm) |
|---|---|---|---|---|---|---|
| 12 | 4-hydroxyphenyl | PMB | BH | CH₂CONH₂ | CHCl₃: 3325, 1793, 1722, 1705, 1615 | CDCl₃ + CD₃OD: 3.45 (s, 3H) 3.75 (s, 3H) 4.16 (br s, 2H) 4.42 (br s, 2H) 4.58 (s, 1H) 4.87 (br s, 2H) 5.02 (s, 1H) 5.10 (br s, 2H) 6.65~7.62 (m, 18H) |
| 13 | 4-hydroxyphenyl | H | H | CH₂CH₂CONH₂ | Nujol: 1788, 1710, 1678, 1176 | CD₃SOCD₃: 2.73 (t, J = 7.5Hz, 2H) 3.19, 3.38 (2 × s, 3H) 3.38 (s, 1H) 4.22~4.60 (m, 2H × 3) 4.61, 4.64 (2 × s, 1H) 4.99 (s, 1H) 6.67, 7.13 (ABq, J = 8Hz, 4H) |
| 14 | 4-hydroxyphenyl | PMB | BH | CH₂CH₂CONH₂ | CHCl₃: 3320, 1790, 1722, 1690, 1251 | CDCl₃: 2.45~2.8 (br, 2H) 3.42 (s, 3H) 3.67 (s, 3H) 4.0~4.6 (m, 2H × 3) 4.92 (s, 1H) 5.02 (s, 2H) 6.53~7.5 (m, 20H) 7.8 (br, 1H) |
| 15 | 4-hydroxyphenyl | H | H | CH₂CH₂N(CH₃)₂·CF₃COOH | Nujol: 1782, 1715, 1673, 1200 | CD₃SOCD₃: 2.78 (s, 6H) 3.18, 3.38 s (2 × s, 3H) 3.55 (t, J = 7Hz, 2H) 4.23 (s, 2H) 4.57 (t, J = 7Hz, 2H) 4.68 (s, 2H) 5.03 (s, 1H) 6.70, 7.13 (ABq, J = 8Hz, 4H) |

TABLE I-continued

[Structure: R¹CHCONH-/COOR²-OCH₃-β-lactam-CH₂S-C(COOR⁴)=... with thiadiazole ring N=N-N-R³]

| Compd. No. | R¹ | R² | R⁴ | R³ | IR ν(cm⁻¹) | NMR δ(ppm) |
|---|---|---|---|---|---|---|
| 16 | 4-HO-C₆H₄- | H | H | CH₂CH₂SO₂NH₂ | KBr: 3380, 3270, 1780, 1720, 1515, 1335, 1150 | CD₃OD: 3.38, 3.50 (2 × s, 3H); 3.70 (t, J = 7Hz, 2H); 4.23 (br s, 2H); 4.43~4.90 (m, 5H); 5.03 (s, 1H); 6.75, 7.25 (ABq, J = 9Hz, 4H) |
| 17 | 4-HO-C₆H₄- | PMB | BH | CH₂CH₂SO₂NH₂ | CHCl₃: 1795, 1725, 1515, 1160 | CDCl₃ + CD₃OD: 3.38, 3.42 (2 × s, 3H); 3.57 (t, J = 6Hz, 2H); 3.37 (s, 3H); 4.17 (br s, 2H); 4.45 (br s, 2H); 4.57 (s, 1H); 4.60 (t, J = 6Hz, 2H); 4.98 (s, 1H); 5.07 (s, 2H); 6.60~7.50 (m, 19H) |
| 18 | 4-PMB-O-C₆H₄- | PMB | BH | CH₂CH₂N(CH₃)₂ | CHCl₃: 3400, 1790, 1725, 1705, 1245 | CDCl₃: 2.18 (s, 6H); 2.65 (t, J = 6.5Hz, 2H); 3.47, 3.50 (2 × s, 3H); 3.77 (s, 3H); 3.80 (s, 3H); 4.20 (t, J = 6.5Hz, 2H); 4.27 (s, 2H); 4.57 (s, 2H); 4.97 (s, 1H); 5.00 (s, 1H); 5.12 (s, 1H); 6.73~7.70 (m, 24H) |

TABLE I-continued
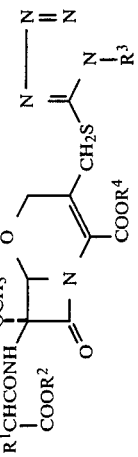
| Compd. No. | R¹ | R² | R⁴ | R³ | IR ν(cm⁻¹) | NMR δ(ppm) |
|---|---|---|---|---|---|---|
| 19 | (tetrahydropyranyloxy-phenyl) | PMB | BH | CH₂CH₂O-PhCH₂OCO | CHCl₃: 3390, 3305, 1782, 1740, 1715, 1610 | CDCl₃: 1.66~1.86 (m, 8H) 3.43, 3.45 (2 × s, 3H) 3.75 (s, 3H) 4.17~4.55 (m, 9H) 4.99 (s, 1H) 5.10 (s, 4H) 5.38 (br s, 1H) 6.67~7.74 (m, 25H) |
| 20 | (4-hydroxy-3-fluorophenyl) | Na | Na | CH₂CH₂OH | Nujol: 3330, 3150, 1765, 1675, 1600 | D₂O (TMS ext. ref.): 3.94, 4.00 (2 × s, 3H) 4.33~4.80 (m, 5H) 4.92 (m, 2H) 4.97 (br s, 2H) 5.56, 5.58 (2 × s, 1H) 7.03~7.82 (m, 3H) |
| 21 | (4-hydroxy-3-fluorophenyl) | H | H | CH₂CH₂OH | R1 = 0.519 (EtOAc:AcOH: H₂O = 5:1:1) | |
| 22 | (4-hydroxy-3-fluorophenyl) | H | H | CH₂CONH₂ | Nujol: 3300, 3175, 1780, 1690, 1630 | CDCl₃ + CD₃OD: 3.50, 3.54 (2 × s, 3H) 4.48 (br s, 2H) 4.83 (s, 1H) 5.02 (br s, 3H) 6.37~7.54 (m, 3H) |

TABLE I-continued

Structure:

R$^1$CHCONH with OCH$_3$ on β-lactam, COOR$^2$, N-substituted β-lactam with CH$_2$O-C(=CH$_2$S-tetrazole-R$^3$)-COOR$^4$, where the tetrazole is a 1,2,3-thiadiazole/tetrazole ring (N=N-N-R$^3$).

| Compd. No. | R$^1$ | R$^2$ | R$^4$ | R$^3$ | IR ν(cm$^{-1}$) | NMR δ(ppm) |
|---|---|---|---|---|---|---|
| 23 | 3-fluoro-4-methylphenol (OH) | H | H | CH$_2$CH$_2$N(CH$_3$)$_2$ | Nujol: 1780, 1678, 1202 | CD$_3$SOCD$_3$ + CD$_3$OD: 2.66 (s, 6H) 3.33, 3.42 (2 × s, 3H) 3.42 (t, J = 7Hz, 2H) 4.24 (s, 2H) 4.56 (br, 2H) 4.61 (t, J = 7Hz, 2H) 4.88, 4.90 (2 × s, 1H) 5.03, 5.06 (2 × s, 1H) 6.55 (d, J = 8Hz, 1H) 6.62 (d, J = 3Hz, 1H) 7.78 (dd, J = 3Hz, J = 8Hz, 1H) |
| 24 | 3-fluoro-4-methylphenyl O—PMB | PMB | BH | CH$_2$CH$_2$OH |  | CDCl$_3$: 3.47 (br s, 3H) 3.70 (s, 3H) 3.74 (s, 3H) 3.80~3.91 (m, 2H) 4.05~4.28 (m, 4H) 4.42 (br s, 2H) 4.83 (s, 1H) 4.89 (s, 2H) 4.98 (s, 1H) 5.08 (s, 2H) 6.50~7.60 (m, 21H) 7.80 (d, 1H, 7.5Hz) |
| 25 | 3-fluoro-4-methylphenyl O—PMB | PMB | BH | CH$_2$CONH$_2$ | CHCl$_3$: 3400, 1785, 1720, 1700, 1610 | CDCl$_3$: 3.44 (s, 3H) 3.71 (s, 3H) 3.75 (s, 3H) 4.30~4.47 (m, 3H) 4.69 (br s, 2H) 4.86 (br s, 4H) 4.93 (s, 1H) 5.08 (s, 2H) 6.57~7.59 (m, 19H) 7.89 (d, J = 6Hz, 1H) |

TABLE I-continued

R¹CHCONH, OCH₃ structure with COOR², β-lactam, CH₂S-C(=N-N=N-R³)-COOR⁴

| Compd. No. | R¹ | R² | R⁴ | R³ | IR ν(cm⁻¹) | NMR δ(ppm) |
|---|---|---|---|---|---|---|
| 26 | 3-fluoro-4-(PMB-O)-phenyl | PMB | BH | CH₂CH₂N(CH₃)₂ | | CDCl₃:<br>2.17 (s, 6H)<br>2.67 (t, J = 7.5 Hz, 2H)<br>3.48 (s, 3H)<br>3.74 (s, 3H)<br>3.79 (s, 3H)<br>4.18 (t, J = 7.5 Hz, 2H)<br>4.24 (s, 2H)<br>4.51 (s, 2H)<br>4.79, 4.82 s (2 × s, 1H)<br>4.93 (s, 2H)<br>5.00 (s, 2H)<br>5.10 (s, 2H)<br>6.6~7.62 (m, 23H) |
| 27 | thienyl | Na | Na | CH₂CH₂OH | KBr:<br>3395<br>1765<br>1675<br>1602<br>1508 | D₂O (TMS ext. ref.):<br>3.92, 3.97 (2 × s, 3H)<br>4.43 (t, J = 5Hz, 2H)<br>4.97 (m, 4H)<br>5.58 (s, 1H)<br>7.58 (d, J = 4Hz, 1H)<br>9.50 (m, 2H) |
| 28 | thienyl | H | H | CH₂CH₂OH | 3450<br>3290<br>1780<br>1717<br>1636<br>1516 | CD₃COCD₃:<br>3.37, 3.47 (2 × s, 3H)<br>3.97 (t, J = 5Hz, 2H)<br>4.30 (s, 2H)<br>4.43 (t, J = 5Hz, 2H)<br>4.96 (s, 1H)<br>5.07 (s, 1H)<br>5.17 (br s, 3H)<br>7.23 (m, 1H)<br>7.40 (m, 2H)<br>8.37 (m, 1H) |
| 29 | thienyl | BH | BH | CH₂CH₂O-OCOCH₂Ph | CHCl₃:<br>1790<br>1745<br>1722<br>1600 | CD₃COCD₃:<br>3.33, 3.38 (2 × s, 3H)<br>4.14 (ABq, J = 14Hz, 2H)<br>4.50 (s, 6H)<br>5.03 (s, 3H)<br>5.13 (s, 1H)<br>6.82 (s, 1H)<br>6.87 (s, 1H)<br>7.03~7.76 (m, 18H)<br>8.33 (s, 1H) |

What we claim is:

1. A compound of the formula

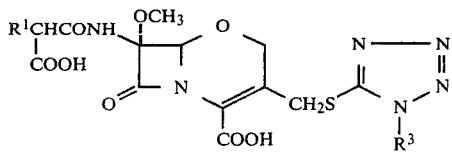

wherein $R^1$ is a member selected from the group consisting of ethyl, p-hydroxyphenyl, 2-fluoro-4-hydroxyphenyl and thien-3-yl, and $R^3$ is a member selected from the group consisting of 2-dimethylaminoethyl, 2-hydroxyethyl, carbamoylmethyl, 2-carbamoylethyl and 2-sulfamoylethyl, or an alkali metal salt thereof.

2. A compound according to claim 1 wherein $R^1$ is p-hydroxyphenyl and $R^3$ is 2-hydroxyethyl or an alkali metal salt thereof.

3. A compound according to claim 1 wherein $R^1$ is p-hydroxyphenyl and $R^3$ is 2-dimethylaminoethyl or an alkali metal salt thereof.

4. A compound according to claim 1 wherein $R^1$ is 2-fluoro-4-hydroxyphenyl and $R^3$ is 2-hydroxyethyl or an alkali metal salt thereof.

* * * * *